United States Patent [19]

Mitschke et al.

[11] 4,144,291
[45] Mar. 13, 1979

[54] PROCESS FOR THE PREPARATION OF BROMOAROXYL-ALKYL-(β-CHLOROALKYL) PHOSPHATES

[75] Inventors: Karl-Heinz Mitschke, Odenthal; Günther Boehmke, Leverkusen, both of Fed. Rep. of Germany

[73] Assignee: Bayer Aktiengesellschaft, Leverkusen, Fed. Rep. of Germany

[21] Appl. No.: 851,257

[22] Filed: Nov. 14, 1977

[30] Foreign Application Priority Data

Nov. 23, 1976 [DE] Fed. Rep. of Germany ....... 2653094

[51] Int. Cl.$^2$ .............................................. C07F 9/09
[52] U.S. Cl. .................................... 260/986; 260/951
[58] Field of Search ....................................... 260/986

[56] References Cited

PUBLICATIONS

Schulek et al., "Talanta," vol. 1 (1958), pp. 224–237.

Primary Examiner—Anton H. Sutto
Attorney, Agent, or Firm—Plumley and Tyner

[57] ABSTRACT

Process for the preparation of phosphates of the formula

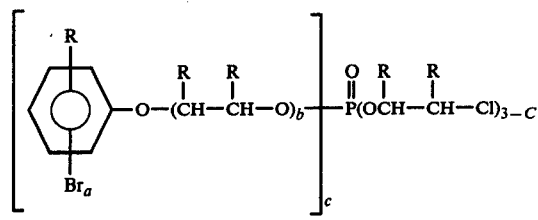

wherein R represents hydrogen, alkoxy or alkyl having 1 to 8 C atoms, perfluoroalkyl having 1 to 8 C atoms, or halogen, a is 0.05 to 3.0, b is 0, 1, 2 or 3 and c is 1 or 2, by brominating the corresponding aroxyalkyl-(β-chloroalkyl) phosphates, characterized in that aroxyalkyl-(β-chloroalkyl) phosphates are reacted at temperatures between about −10° and 80° C. with an approximately equimolar mixture of bromine and chlorine, especially bromine chloride.

4 Claims, No Drawings

PROCESS FOR THE PREPARATION OF BROMOAROXYL-ALKYL-(β-CHLOROALKYL) PHOSPHATES

The present invention relates to a process for the preparation of brominated aroxyalkyl-(β-chloroalkyl) phosphates. The process according to the invention is particularly suitable for the preparation of aroxyalkyl-(β-chloroalkyl) phosphates which have a low bromine content (up to 3.0 bromine atoms per phenyl nucleus).

Bromoaroxyalkyl-(β-chloroalkyl phosphates, amongst which bis-(bromoaroxyalkyl)-β-chloroalkyl phosphates, bromoaroxy-bis-(β-chloroalkyl) phosphates and mixtures thereof are to be understood, are used for flameproofing combustible substances, particularly plastics and fibres (compare, for example, U.S. Pat. No. 3,816,143 and DT-OS (German Published Specification) No. 2,346,428).

The reactions of bromoaroxyalkanols (which can be prepared from bromophenols and alkylene oxides) with phosphorus oxychloride and alkylene oxides are described (U.S. Pat. No. 3,816,143 and Houben-Weyl, Methoden der Organischen Chemie (Methods of Organic Chemistry), volume 12/2, pages 319 and 337) for the preparation of the bromoaroxyalkyl-(β-chloroalkyl phosphates. It is a disadvantage, however, that bromophenols are compounds which are accessible with difficulty and, in particular, toxic, and that, in the conventional method for the preparation of bromophenols from bromine, the hydrogen bromide which is formed as a by-product must be recovered by oxidation in a special apparatus to give bromine, which is valuable.

It was the object of the present invention to provide a simple and economical process for the preparation of brominated aroxyalkyl-(β-chloroalkyl) phosphates.

The subject of the present invention is a process for the preparation of brominated aroxyalkyl-(β-chloroalkyl) phosphates of the general formula

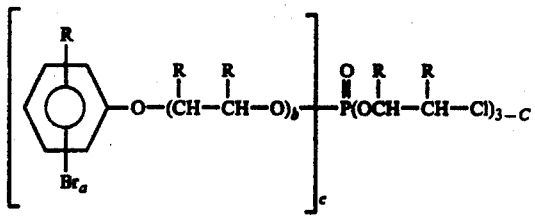

wherein
R represents hydrogen, an alkoxy or alkyl radical having 1 to 8 C atoms, a perfluoroalkyl radical having 1 to 8 C atoms or halogen,
a can be 0.05 to 3.0, preferably 0.1 to 2.5,
b can be 0, 1, 2 or 3 and
c can be 1 or 2,
by brominating the corresponding aroxyalkyl-(β-chloroalkyl) phosphates, which is characterised in that aroxyalkyl-(β-chloroalkyl) phosphates are reacted at temperatures between about −10° and 80° C with an approximately equimolar mixture of bromine and chlorine, especially with bromine chloride.

It has been found that the bromination of aroxyalkyl-(β-chloroalkyl) phosphates can be carried out particularly advantageously using mixtures of bromine and chlorine, especially using bromine chloride. Above all, it was surprising that the brominations can be carried out selectively, even at relatively low temperatures. Whilst in general brominations with bromine are carried out at 80°–100° C., this can be carried out in accordance with the invention at substantially lower temperatures, without a significant chlorine substitution taking place and without the presence of catalysts being necessary. Furthermore, it was surprising that no splitting of either the ester grouping or the ether grouping as a result of the hydrogen chloride which forms during the reaction could be observed.

The process according to the invention is carried out by introducing bromine chloride or bromine and chlorine, without the addition of catalysts, into the corresponding aroxyalkyl-(β-chloroalkyl) phosphates whilst stirring and cooling. The brominations are carried out at temperatures between about −10° and 80° C., preferably at room temperature, over a period of time of about 0.5 to 7 hours. The reaction product is then freed, optionally in vacuo, from volatile constituents, such as, for example, hydrogen chloride, bromine chloride or bromine and chlorine, and is washed with water which can optionally contain a reducing agent, such as, for example hydrazine, sulphur dioxide or a sulphite, and then with aqueous alkali, for example sodium hydroxide solution, and water. It is also possible to convert, by means of bromine chloride or bromine and chlorine, the phosphoric acid aroxyalkyl ester-chlorides resulting from aroxyalkanols and phosphorus oxychloride into the corresponding phosphoric acid bromoaroxyalkyl ester-chlorides and to react the latter further with alkylene oxides in a known manner.

The process can also be carried out in suitable solvents, such as, for example, halogenohydrocarbons. This variant is expedient in the case of higher-melting or highly viscous products; in the case of liquid or low-melting products it is preferable to carry out the reaction without a solvent. The solvent can be mixed with the bromine chloride or bromine and chlorine, or can be initially taken together with the corresponding aroxyalkyl-(β-chloroalkyl) phosphates.

Depending on th degree of bromination desired, the quantity of bromine employed per phenyl nucleus should be approximately between 0.05 and 3, preferably between 0.1 and 2.5, bromine atoms.

The process according to the invention can be carried out both continuously — generally in several stages in a reaction cascade — and discontinuously. In the discontinuous process it is preferable to introduce bromine chloride or bromine and chlorine into the corresponding aroxyalkyl-(β-chloroalkyl) phosphates.

The process according to the invention is mainly suitable for the preparation of aroxyalkyl-(β-chloroalkyl) phosphates of low bromine content. Thse compounds of low bromine content (having a degree of bromination of up to 3, preferably up to 2.5, bromine atoms per phenyl nucleus) cannot be prepared economically from bromophenols, alkyl aroxides and phosphorus oxychloride by the processes hitherto known. These aroxyalkyl-(β-chloroalkyl) phosphates of low bromine content, which are distinguished because of their properties (low melting point and absence of odour), can now be prepared, in accordance with the invention, in an advantageous manner.

The process according to the invention will be illustrated in greater detail by means of some examples (unless otherwise specified, % figures denote % by weight)

EXAMPLE 1

2,072 g (15 mols) of phenoxyethanol are added dropwise at 20° C. to 3,834 g (25 mols) of phosphorus oxychloride in a three-necked flask which is equipped with a stirrer, a reflux condenser and an internal thermometer. The reaction mixture is subsequently stirred for approximately 4 hours and the excess phosphorus oxychloride is then removed at 20 to 70° C. (approximately 1 mm Hg). 1,361 g (30.9 mols) of ethylene oxide are added dropwise at approximately 70° C., if necessary whilst cooliing, to the 3,797 g (14.9 mols) of the phosphoric acid-ester-dichloride which is formed and to which 18 ml of titanium tetrachloride are added. When the reaction is complete, the excess ethylene oxide is removed at 50° to 70° C. in vacuo (1 mm Hg). The titanium catalyst required for the ethoxylation is removed by washing with 3 N hydrochloric acid and the resulting phosphoric acid phenoxyethyl-ester-bis-(2-chloroethyl ester) (5,045 g) is dried in vacuo.

4,385 g (38 mols) of bromine chloride are passed into 4,345 g (12.7 mols) of this triester at 20° to 30° C., whilst cooling and stirring. The hydrogen chloride formed, with which traces of bromine chloride, or bromine and chlorine, are mixed, is passed into water containing sodium sulphite. After the addition of bromine chloride, the hydrogen chloride and bromine chloride, or bromine and chlorine, dissolved in the crude product are removed in vacuo at 20° to 70° C. The final purification of the product is carried out by washing with 2% strength sodium sulphite solution, 2% strength sodium hydroxide solution and then, several times, with ion-free water. After drying in vacuo at 70° to 80° C., 6,755 g of the compound having the average composition

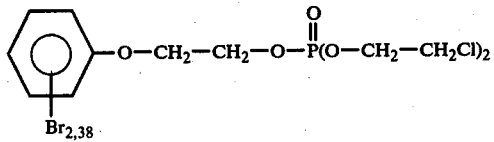

are obtained.

EXAMPLE 2

1,800 g of the compound having the average composition

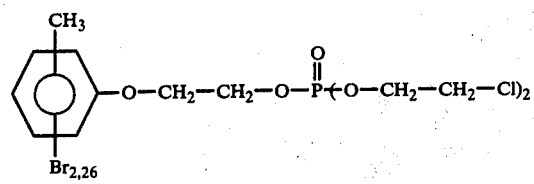

are obtained, analogously to the experimental procedure of Example 1, from 540 g (3.55 mols) of tolueneoxyethanol, 1,089 g (7.1 mols) of phosphorus oxychloride, 333 g (7.5 mols) of ethylene oxide and 4.3 ml of titanium tetrachloride, subsequently brominating with 1,177 g (10.2 mols) of bromine chloride.

EXAMPLE 3

The compound from Example 1

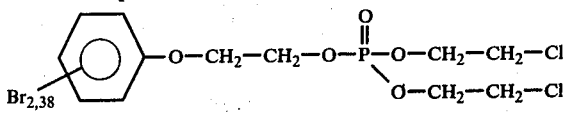

is formulated in isopropyl alcohol to give a 12.5% strength solution. A polyester fabric having a weight of approximately 300 g per square meter is padded with this solution. The squuezing-off effect should correspond to a pick-up of 80% of the weight of the goods (that is to say 10% of flameproofing agent). The fabric is briefly dried at 100° C. and is then heated at 160° C. for 10 minutes. After this treatment the fabric contains 8 to 9% of the above compound.

The fabric passes the vertical burning test in accordance with DIN 53,096 immediately after the condensation and also after 10 machine washes at 60° C. using a commercially available domestic detergent.

EXAMPLE 4

An emulsifiable formulation of the compound according to Example 1 is obtained by means of the following mixture: 50% of substance according to Example 1, 20% of trichlorobenzene, 20% of xylene, 4% of Ca dodecylbenzenesulphonate and 6% of benzylphenol polyglycol ether (containing 15 mols of ethylene oxide.)

A polyester fabric is boiled for 60 minutes at a liquor ratio of 1:25, in a bath which contains 8 g/l of the above flameproofing formulation in an emulsion.

The fabric is then rinsed for 10 minutes at 40° to 50° C. with 1 g/l of sodium oleylsulphate.

The fabric passes the burning test in accordance with DIN 53,096 initially and after 10 machine washes.

The emulsifiable formulation can, of course, also be applied in accordance with the instructions of Example 3 by padding with 300 g/l, squeezing-off to an 80% pick-up, drying intermediately and carrying out the condensation. After this fixing, the fabric is rinsed and then tested.

We claim:

1. Process for the preparation of brominated aroxyalkyl-($\beta$-chloroalkyl) phosphates of the general formula

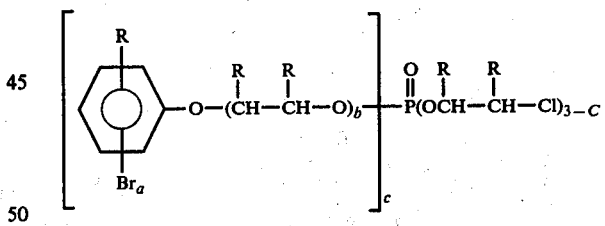

wherein

R represents hydrogen, an alkoxy or alkyl radical having 1 to 8 C atoms, a perfluoroalkyl radical having 1-8 C atoms, or halogen, a can assume values of 0.05 to 3.0, b can be 0, 1, 2 or 3 and c can be 1 or 2 by brominating the corresponding aroxyalkyl-($\beta$-chloroalkyl) phosphates, characterised in that aroxyalkyl-($\beta$-chloroalkyl) phosphates are reacted at temperatures between about −10 and 80° C. with an approximately equimolar mixture of bromine and chlorine, especially bromine chloride.

2. Process according to claim 1, characterised in that the bromination is carried out in the presence of organic solvents.

3. Process according to claim 1 or 2, characterised in that the degree of bromination is 0.1 to 2.5 bromine atoms per phenyl nucleus.

4. The process of claim 1 in which R is hydrogen, methoxy, methyl, trifluoromethyl, or halogen.

* * * * *